United States Patent
Degen et al.

(10) Patent No.: US 10,660,647 B2
(45) Date of Patent: May 26, 2020

(54) DEVICE FOR POSITIONING AND RELEASING A CLOSURE IMPLANT FOR CLOSING THE LEFT ATRIAL APPENDAGE

(71) Applicant: BIOTRONIK AG, Buelach (CH)

(72) Inventors: Nicolas Degen, Beringen (CH); Jens Ulmer, Kuesnacht (CH)

(73) Assignee: BIOTRONIK AG, Buelach (CH)

( * ) Notice: Subject to any disclaimer, the term of this patent is extended or adjusted under 35 U.S.C. 154(b) by 247 days.

(21) Appl. No.: 15/813,962

(22) Filed: Nov. 15, 2017

(65) Prior Publication Data

US 2018/0132861 A1    May 17, 2018

(30) Foreign Application Priority Data

Nov. 15, 2016  (EP) .................................. 16198899

(51) Int. Cl.
*A61F 2/958* (2013.01)
*A61B 17/12* (2006.01)
*A61B 17/00* (2006.01)

(52) U.S. Cl.
CPC .. *A61B 17/12145* (2013.01); *A61B 17/12031* (2013.01); *A61B 17/12122* (2013.01); *A61B 17/12168* (2013.01); *A61B 17/12172* (2013.01); *A61B 17/12177* (2013.01); *A61B 2017/00867* (2013.01); *A61B 2017/12054* (2013.01); *A61B 2017/12095* (2013.01)

(58) Field of Classification Search
CPC .............. A61B 17/12; A61B 17/00575; A61B 17/12145; A61B 17/12031; A61B 17/12168; A61B 17/12122; A61B 2/06; A61B 2/95; A61B 2/962; A61B 2/12118; A61B 17/0057; A61B 17/50; A61F 2/06; A61F 2/95; A61F 2/962; A61F 2/12118; A61F 2/958; A61F 2/07; A61F 2/966
See application file for complete search history.

(56) References Cited

U.S. PATENT DOCUMENTS

| 8,388,672 | B2 * | 3/2013 | Khairkhahan | A61F 2/2487 |
| | | | | 623/1.11 |
| 2002/0099431 | A1 * | 7/2002 | Armstrong | A61F 2/95 |
| | | | | 623/1.11 |

(Continued)

FOREIGN PATENT DOCUMENTS

| EP | 2074953 A1 | 7/2009 |
| WO | 2010024801 A1 | 3/2010 |
| WO | 2012003317 A1 | 1/2012 |

OTHER PUBLICATIONS

Tanguy Roudaut, European Search Report for Application No. 17201530.7, dated Feb. 8, 2018.

(Continued)

*Primary Examiner* — Vi X Nguyen
(74) *Attorney, Agent, or Firm* — Greer, Burns & Crain, Ltd; Steven P. Fallon (57) ABSTRACT

A device for closing the left atrial appendage. The device has a flexible and elongate pulling element fixed to a flexible material layer connected fixed to a self-expanding stent. The closure implant can be drawn back into the lumen of a catheter by the pulling element, and in so doing the stent framework can be transferred into a compressed state. The device enables a monitored and controllable release of the closure implant.

14 Claims, 12 Drawing Sheets

(56) References Cited

U.S. PATENT DOCUMENTS

| | | |
|---|---|---|
| 2003/0181942 A1 | 9/2003 | Sutton et al. |
| 2010/0234878 A1 | 9/2010 | Hruska et al. |
| 2013/0138138 A1 | 5/2013 | Clark et al. |
| 2013/0218193 A1 | 8/2013 | Erzberger et al. |
| 2014/0135817 A1 | 5/2014 | Tischler et al. |
| 2014/0277074 A1 | 9/2014 | Kaplan et al. |

OTHER PUBLICATIONS

Tanguy Roudaut, European Search Report for Application No. 16198899.3, dated Feb. 23, 2017.

\* cited by examiner

DEVICE FOR POSITIONING AND RELEASING A CLOSURE IMPLANT FOR CLOSING THE LEFT ATRIAL APPENDAGE

PRIORITY CLAIM

This application claims priority under 35 U.S.C. § 119 and all applicable statutes and treaties from prior European Application EP 16198899.3, filed Nov. 15, 2016, which application is incorporated by reference herein.

FIELD OF THE INVENTION

A field of the invention concerns closure implants for closing the left atrial appendage of a patient's heart, and particularly concerns a device for positioning and releasing such closure implants.

BACKGROUND

Closure implants (aka occlusion devices) for closing the left arterial appendage are described, for example, in Tischler et al., US Published Application No. 2014/0135817, Sutton et al., US Published Application No. 2003/0181942 and Clark et al., US Published Application No. 2013/0138138. These applications seek to respectively provide an occlusion device that controls thrombus formation within the left atrial appendage, a delivery system that provides for delivery through geometrically complex vascular paths, and an occlusion device with improved circumferential strength and without foreshortening or excessive distortion.

Each of these systems mentioned in the previous paragraph includes a self-expanding support frame. Self-expanding systems of this kind are generally based on what is known as the pull-back principle, in which an outer catheter sleeve forces the implant into a collapsed form and releases it again by retraction of the outer sleeve. Due to the shaping of the closure implants (usually barrel-shaped), the release cannot be controlled as accurately by the pull-back principle, since the closure implant can spring out suddenly when released to an extent of approximately two thirds. Since the atrial appendage is an extremely fragile tissue, there is a high risk of injury by an uncontrolled release of a closure implant.

Figure 1:
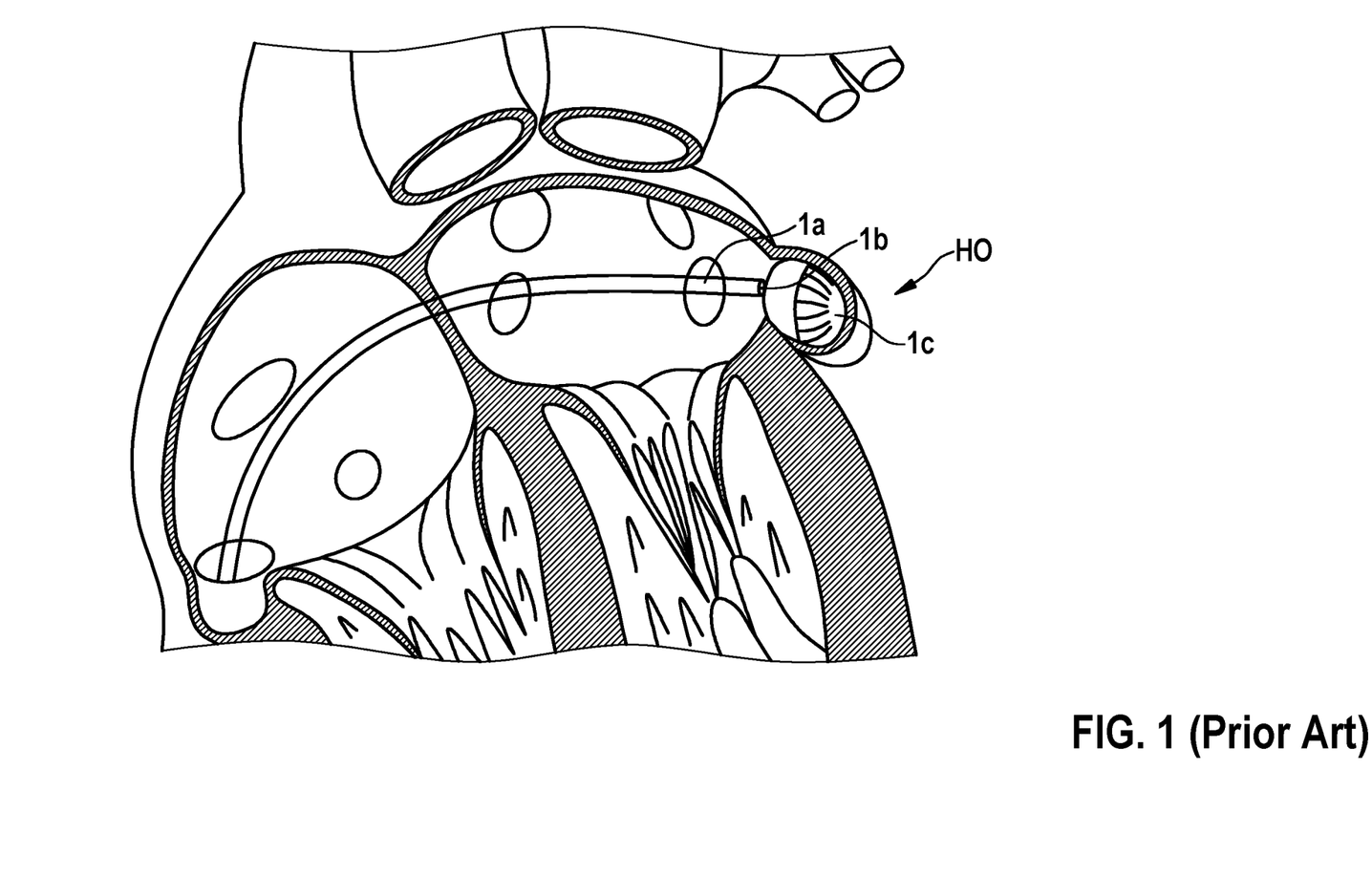
FIG. 1 shows a closure implant according to the prior art.

According to FIG. 1 the current systems and closure implants 1c are also firmly connected by a screw 1b and in particular a guide wire to the catheter 1a. This hinders the checking of successful placement insofar as the fixing of the implant in the atrial appendage tissue cannot be sufficiently examined (for example a secure fit of the implant after placement in the atrial appendage can be determined on the basis of a pull test).

SUMMARY OF THE INVENTION

A preferred embodiment of the invention provides a device for positioning and releasing a closure implant for closing the left atrial appendage. The device includes a closure implant configured for closing the left atrial appendage. The closure implant has a self-expandable stent framework, which can be automatically expanded from a compressed state into an expanded (for example unfolded) state. The closure implant has a flexible material layer fixed to the stent framework. The material layer in the expanded state of the stent framework is stretched. A catheter with a lumen receives the closure implant in the compressed state of the stent framework. The closure implant is released from the lumen by being slid out, and in so doing the stent framework is transferred into the expanded state. The device further includes a flexible and elongate pulling element fixed to the flexible material layer, so that the closure implant can be drawn back into the lumen of the catheter by means of the pulling element, and in so doing the stent framework can be transferred into the compressed state. Devices of the invention enable a monitored and controllable release of the closure implant.

BRIEF DESCRIPTION OF THE DRAWINGS

Further features and advantages of the invention will be explained in the description of the drawings of exemplary embodiments of the invention with reference to the drawings, in which.

DETAILED DESCRIPTION OF THE PREFERRED EMBODIMENTS

A stretched material layer in the expanded state of the stent framework is understood within the scope of this application to mean a material layer which substantially fills or covers the cross-sectional area of the stent framework. Here, the term stretched is not to be understood in the narrow sense as being "under tension", but instead the term stretched means a planar, substantially unfolded state of the material layer.

It is provided in accordance with preferred embodiments of the invention that the device has a flexible (in particular limp) elongate pulling element fixed to the flexible material layer, so that the closure implant can be drawn back into the lumen by means of the pulling element, and in so doing the stent framework can be transferred into the compressed state.

The ability of the stent framework to self-expand can be provided for example by a material property of the stent framework, for example a resilient restoring force or superelasticity. The stent framework is preferably made of a shape-memory alloy, in particular nitinol. Another mechanical principle of operation can also provide the automatic expansion. The stent framework is in particular held in its compressed state by its arrangement in the lumen of the catheter and unfolds as soon as it is slid out from the lumen (through an opening of the catheter, for example by a means guided in the lumen suitable for sliding out the closure implant).

In accordance with a preferred embodiment of the device according to the invention, it can be provided that the pulling element comprises a cord or a thread. In particular, the pulling element can be composed of a number of strands, wherein a strand of this kind can be formed for example by a cord or a thread.

In a preferred embodiment of the invention, the pulling element is embodied as a plastic thread, preferably made of polyethylene terephthalate (PET), polyamide (PA) and/or polypropylene (PP), wherein the thread can consist both of an individual fibre (strand) and of a plurality of individual and interconnected fibres (strands).

In accordance with a preferred embodiment of the device according to the invention, it is also provided that the material layer consists of a fabric, wherein the pulling element is guided through the fabric of the material layer.

In this preferred embodiment of the invention the material layer consists of a fabric which is formed in such a way that the pulling element can be guided through the fabric. In this embodiment of the invention the material layer is selected in such a way that the pulling element can be guided through the material layer similarly to a thread when sewing clothes.

It is also provided in accordance with a preferred embodiment of the device according to the invention that the pulling element has a first and a second end, wherein the pulling element has a thickened portion between the two ends, so that the pulling element can be completely pulled out from the material layer by pulling on the second end, and so that the thickened portion, as the pulling element is pulled at the first end, impacts against the material layer such that the released closure implant can be pulled back into the lumen of the catheter in the proximal direction via the material layer (here, the thickened portion pulls on the material layer/fabric and the material layer pulls on the stent framework).

The proximal direction is here the direction in which the closure implant can be pulled back into the catheter or into the lumen, i.e. can be moved away from the atrial appendage. Accordingly, the proximal end of the stent framework (arranged in the catheter) is the end which is further distanced from the atrial appendage (the stent framework is inserted forwards by means of its distal end into the atrial appendage). The direction opposite the proximal direction is the distal direction. For this purpose, the stent framework is pushed out from the lumen of the catheter in the distal direction and introduced into the atrial appendage. The above-described thickened portion of the pulling element is arranged on the distal side of the material layer (the thickened portion accordingly entrains the material layer or the stent framework when pulled in the proximal direction).

In the case of a closure implant arranged in the lumen with stent framework in the compressed state, the pulling element thus runs starting from the first end in the lumen to the material layer, is guided there through the through-opening of the material layer, wherein the thickened portion is arranged on the distal side of the material layer (see above), and extends from there, past a peripheral edge region of the material layer, back to the second end.

The pulling element thus can be handled via both ends, wherein suitable actuation means of the device can be coupled to the ends of the pulling element as appropriate, such that the pulling element can be pulled outside the patient's body by way of the actuation means as described above. For this purpose, the two ends of the pulling element can be guided suitably from the lumen of the catheter.

It is also provided in accordance with a preferred embodiment of the device according to the invention that the material layer is a fabric. The material layer can also be another flexible (in particular textile) planar material.

In particular, the material layer or the fabric can consist of a synthetic material, such as polyethylene terephthalate (PET), polyamide (PA), Teflon® and/or polypropylene (PP). These materials are connected as individual fibres or fibre bundles to form a fabric. A fabric of this kid is sold for example under the trade name Dacron®.

In an alternative embodiment the material layer or the fabric can also consist of a natural material, such as pericardial tissue or bacterial cellulose.

In accordance with a preferred embodiment of the device according to the invention it is also provided that the stent framework has a plurality of struts, wherein the struts each have a first end portion and an opposite second end portion, and wherein the first end portions of the struts are connected to one another (in particular are integrally connected to one another), and wherein the second ends are each connected to a peripheral edge region of the material layer.

The struts extend radially outwardly, in particular starting from a common base (the first end portions connected to one another), and at the same time in the axial direction of the stent framework, such that the struts can be moved towards one another in the radial direction in order to produce the compressed state with its second end portions, wherein they come to lie adjacently to the (virtual) axial direction or stent axis.

In this way the second end portions of the struts in the compressed state of the stent framework have a shorter spacing from one another than in the unfolded state, in which the second end portions are distanced from one another in the radial direction in such a way that the material layer fixed thereto is stretched, in particular is stretched taut.

In order to fix said material layer to the stent framework, it is preferably provided in accordance with one embodiment of the device according to the invention that the second end portions each have at least one recess (for example an undercut or eyelet), wherein the peripheral edge region of the material layer is connected to the at least one recess of each second end portion by means of one thread per recess (for example by sewing or knotting).

It is also provided in accordance with one embodiment that the peripheral edge region of the material layer covers the second end portions of the struts at least in part. It is thus ensured that the material layer, by means of the peripheral edge region, can bear against the edge or ostium of the atrial appendage and provide a corresponding sealing effect.

In accordance with a preferred embodiment of the device according to the invention it is also provided that the struts at the second end portions each have a protrusion for anchoring the stent framework in the ostium of the atrial appendage. For this purpose the protrusions can each taper to a point. The protrusions preferably extend (based on an expanded state of the stent framework) in each case starting from the second end portion of a particular strut outwardly in the radial direction of the stent framework.

In accordance with one embodiment of the invention it is also provided that the struts in their particular plane of extent each have a right-hand curvature and then a left-hand curvature, in each case starting from the corresponding first end portion. A goblet shape of the expanded stent framework can hereby be provided, which enables an effective shortening of the stent framework in the axial direction. However, the stent framework in the expanded state can alternatively also taper conically.

In accordance with a preferred embodiment it is also provided that the material layer in the stretched state (i.e. in the case of an expanded stent framework) forms a circular surface of the closure implant for closing the atrial appendage.

In accordance with one aspect of the present invention a further device for positioning and releasing a closure implant for closing the left atrial appendage is also provided, comprising: a closure implant for closing the left atrial appendage, wherein the closure implant has a self-expandable stent framework, which can be expanded automatically from a compressed state into an expanded state, and wherein the closure implant has a flexible material layer fixed to the stent framework, wherein the material layer is stretched in the unfolded state; and a catheter for transporting the closure implant to the site of implantation, wherein the device has at least one flexible (in particular limp) and elongate pulling element, wherein the stent framework can be held in the compressed state by means of the pulling element, and wherein the pulling element is releasable, so that the stent framework can be unfolded.

The corresponding pulling element can be formed as a cord or thread or can comprise a cord or a thread. In a further embodiment a plurality of pulling elements can also be used.

In the further aspect of the present invention it is preferably provided that the stent framework extends in an axial direction or along a stent axis, wherein the stent framework has a plurality of bars extended continuously along the axial direction, which bars run parallel to one another and are each connected by means of stent half-cells to bars that are adjacent in the peripheral direction, wherein the struts of the stent half-cells have a smaller width than the bars, and wherein the bars taper towards their ends, so that a compressed state of the stent framework can be produced for example by a peripheral pulling element arranged centrally on the stent framework (for example by narrowing a loop formed by the pulling elements).

The stent framework can be arranged on a catheter, wherein the pulling elements run in the lumen of the catheter. These pulling elements can be guided out from the catheter/lumen through corresponding through-openings, wherein they are each placed around a bar of the stent framework, so that they can hold the stent framework in its compressed state. The stent framework can then be pushed forwards by means of its distal end into the atrial appendage, wherein the pulling elements are then loosened, so that the stent framework is expanded in the atrial appendage and the material layer fixed to the proximal end of the stent framework is stretched, and in so doing closes the atrial appendage. The pulling elements can then be completely removed via the lumen of the catheter.

Figure 2:
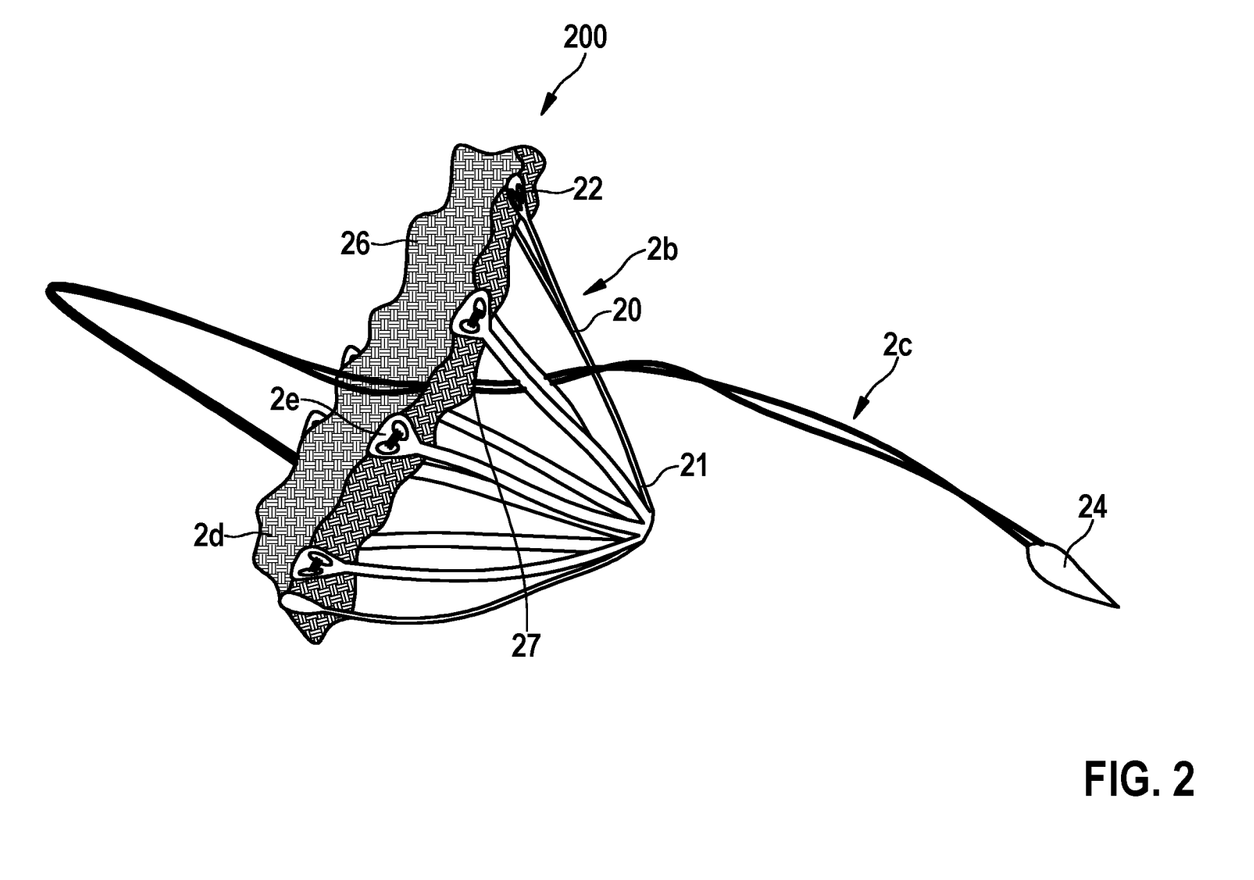
FIG. 2 shows a closure implant according to the invention of a device according to the invention.

FIG. 2, in conjunction with FIGS. 3 to 13, shows a device 10 according to the invention for closing the left atrial appendage HO of a heart, in particular a human heart, which is illustrated schematically for example in FIG. 1. The device 10 has a closure implant 200 for closing the left atrial appendage HO, wherein the closure implant 200 has a self-expandable stent framework 2b, which can be expanded automatically from a compressed state into an expanded state, and wherein the closure implant 200 has a flexible material layer 2d fixed to the stent framework 2b, wherein the material layer 2d is substantially stretched in the expanded state of the stent framework 2b. The stent framework 2b can be formed for example of nitinol or another suitable material.

The device 10 also has a catheter K with a lumen L for receiving the closure implant 200 in the compressed state of the stent framework 2b, wherein the closure implant 200 can be released by being slid out from the lumen L (in the distal direction or to the left in FIG. 8) and the stent framework 2b can be transferred into the expanded state, which is shown for example in FIGS. 2, 3, 4, 5, 6 and 7. It is provided in accordance with the invention that the device 10 has a flexible and in particular limp and elongate pulling element 2c fixed to the flexible material layer 2d, such that the closure implant 200 can be pulled back again into the lumen L of the catheter K by means of the pulling element 2c, and in so doing the stent framework 2b can be transferred into the compressed state (see FIGS. 10 and 11).

In order to push out the closure implant, the device 10 can have a suitable slider (also known as a pusher), which is arranged or can be arranged in the lumen L of the catheter K and is movable in the lumen L (slider not illustrated in the figures for reasons of clarity). For example, the slider can be a polymer lumen, a hypotube, or what is known as a push-wire.

Figure 3:
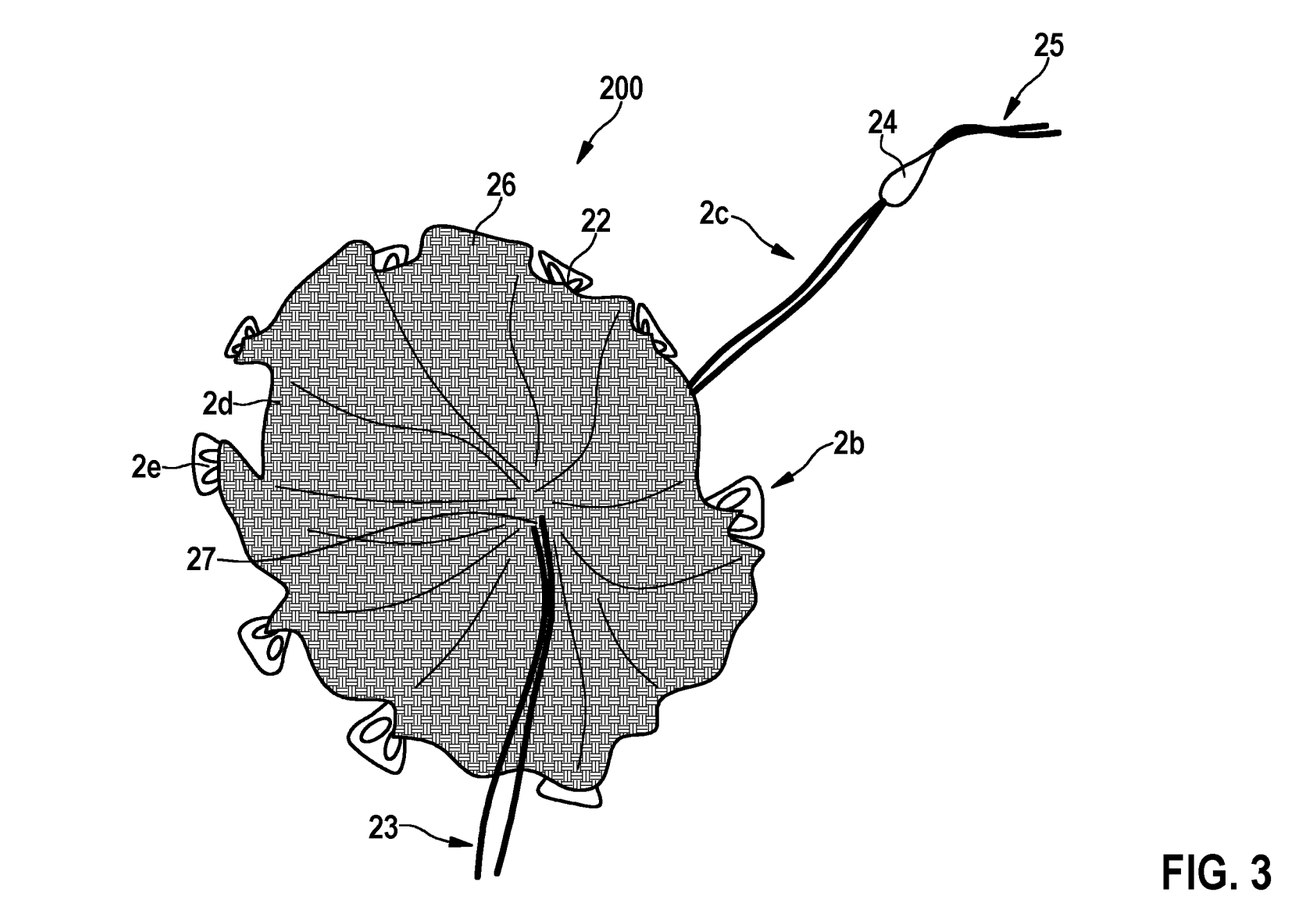
FIG. 3 shows a further view of the closure implant shown in FIG. 2.
Figure 4:
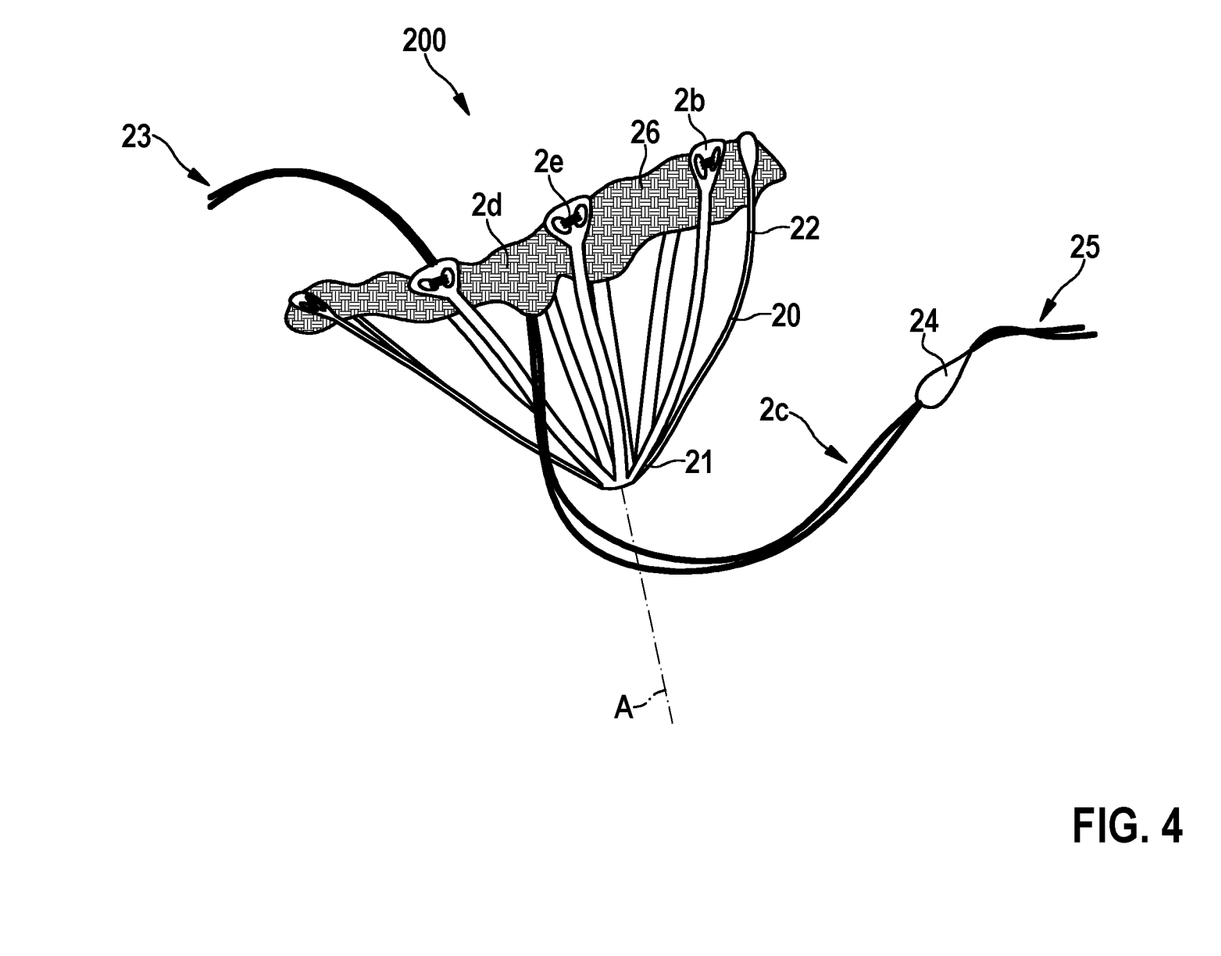
FIG. 4 shows a further view of the closure implant shown in FIGS. 2 and 3.
Figure 5:
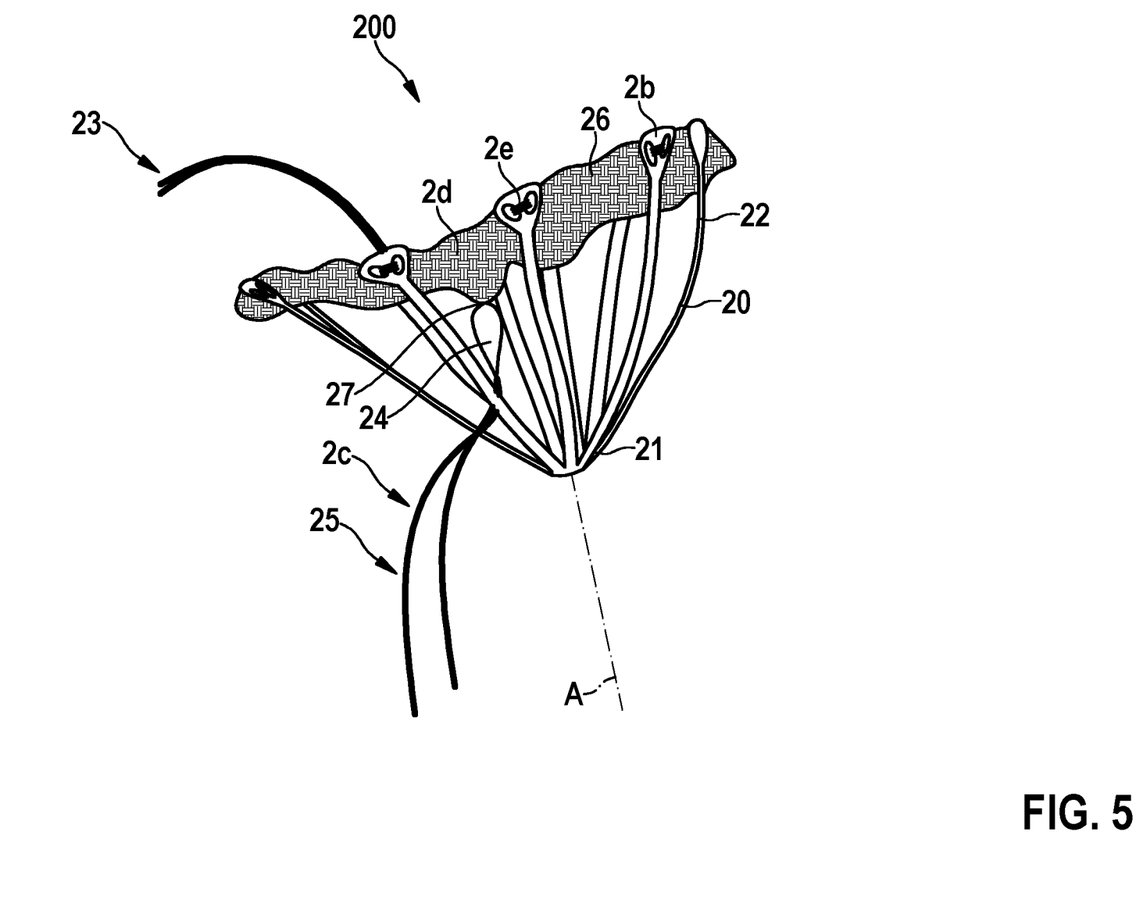
FIG. 5 shows a further view of the closure implant shown in FIGS. 2 to 4.

As shown for example in FIG. 3, the pulling element 2c can have a cord or a thread, wherein the pulling element 2c for example can also have two or more strands, which can each be a cord or a thread.

As can also be seen from FIG. 3, the pulling element 2c is guided through the material layer 2d at the point 27. The pulling element 2c in so doing passes through the material layer 2d similarly to a thread guided through a fabric when clothes are being sewn.

The pulling element 2c here has a first and a second free end 23, 25, wherein the pulling element 2c has a thickened portion 24 between the two ends 23, 25, i.e. a portion of increased outer diameter, so that the pulling element 2c can be pulled out completely from the material layer 2d by pulling on the second end 25, and so that the thickened portion 24, when the pulling element is pulled at the first end 23, impacts against the material layer 2c, so that, when the closure implant 200 is released, the closure implant 200 can be pulled back into the lumen L of the catheter K in the proximal direction via the material layer. The material layer 2d is created in such a way that it is sufficiently elastic to allow the pulling element to be passed through 27. The inner elasticity of the material layer, however, is also sufficiently small to prevent the thickened portion 24 from being guided through the material layer under forces with which the pulling element 2c is usually pulled during its handling. The material layer 2d in particular can be a fabric, where a passage 27 for the pulling element is formed through the structure of the fabric. The space already provided microscopically in the fabric between the individual fibres forming the fabric is widened elastically in order to form the through-opening 27 for the pulling element 2c.

The thickened portion 24 is preferably drop-shaped, wherein the drop tapers in the direction of the second end 25. Following implantation of the closure implant 200, the pulling element can thus be removed from the body more easily between the atrial appendage and closure implant by pulling in the direction of the second end 25.

The pulling element 2c thus can be handled via both ends 23, 25, wherein suitable actuation means of the device can be coupled to the ends 23, 25 as appropriate and are not described here in greater detail.

As can be seen in particular in FIGS. 2 to 7, the stent framework 2b has a plurality of struts 20, wherein the struts 20 each have a first end portion 21 and an opposite second end portion 22, wherein the first end portions 21 of the struts 20 are connected to one another, and wherein the second end portions 22 are each connected to a peripheral edge region 26 of the material layer 2c. Here, the struts 20 run—based on an expanded state of the stent framework 2b—starting from a common base or the first end portions 21 in an axial direction A and in each case in a radial direction perpendicular thereto, so that the struts 20 run away from one another in the direction of the corresponding second end portion 22. In this expanded state the material layer 2d fixed to the second end portions 22 is stretched. In the compressed state of the stent framework 2b, by contrast, the second end portions have a much shorter spacing from one another in the radial direction, so that the material layer 2d is not stretched accordingly.

In order to fix the peripheral edge region 26 of the material layer 2d to the second end portions 22 of the struts 20, the respective end portions 22 in particular each have at least one recess 2e, in particular eyelet, wherein the peripheral edge region 26 of the material layer 2d is connected to the at least one recess 2e or the corresponding strut 20 of each second end portion, preferably by means of one seam or one thread per recess/strut.

The material layer 2d is thus deployed in particular solely by the radial expansion of the stent framework 2b and thus enables the atrial appendage HO to be closed relative to the atrium.

Figure 6:
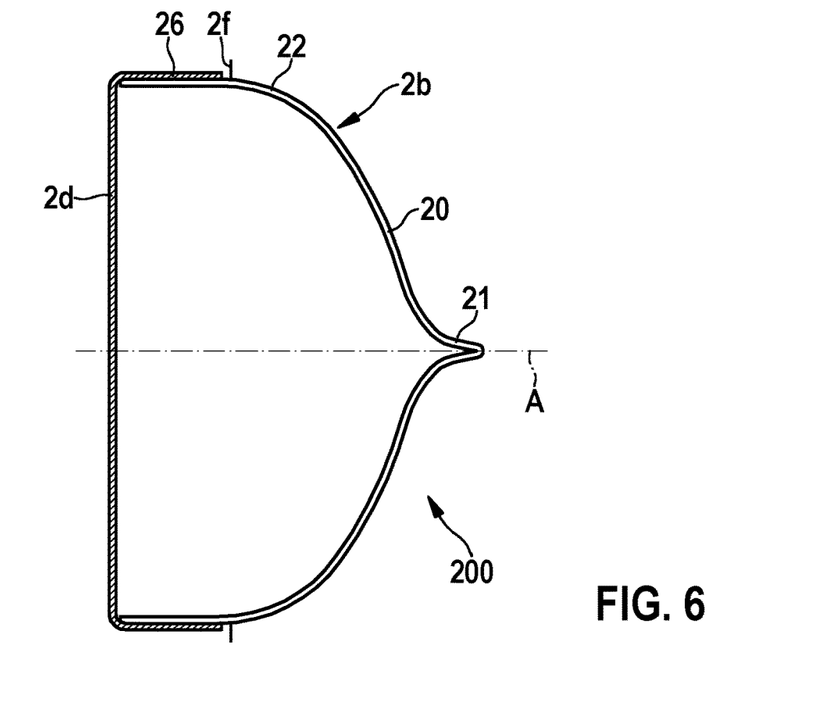
FIG. 6 shows a schematic sectional view of the closure implant shown in FIGS. 2 to 5.
Figure 7:
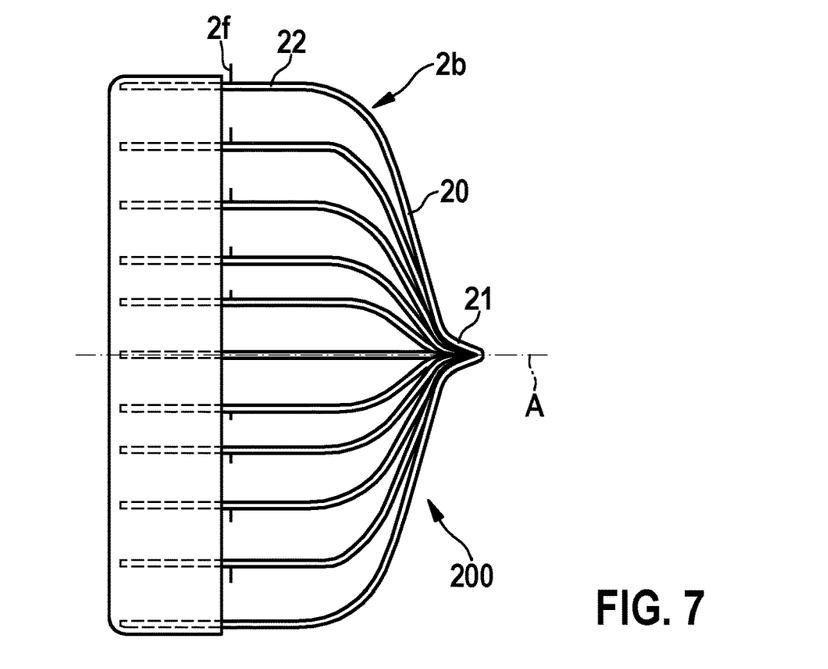
FIG. 7 shows a side view of the closure implant shown in FIG. 6.
Figure 8:
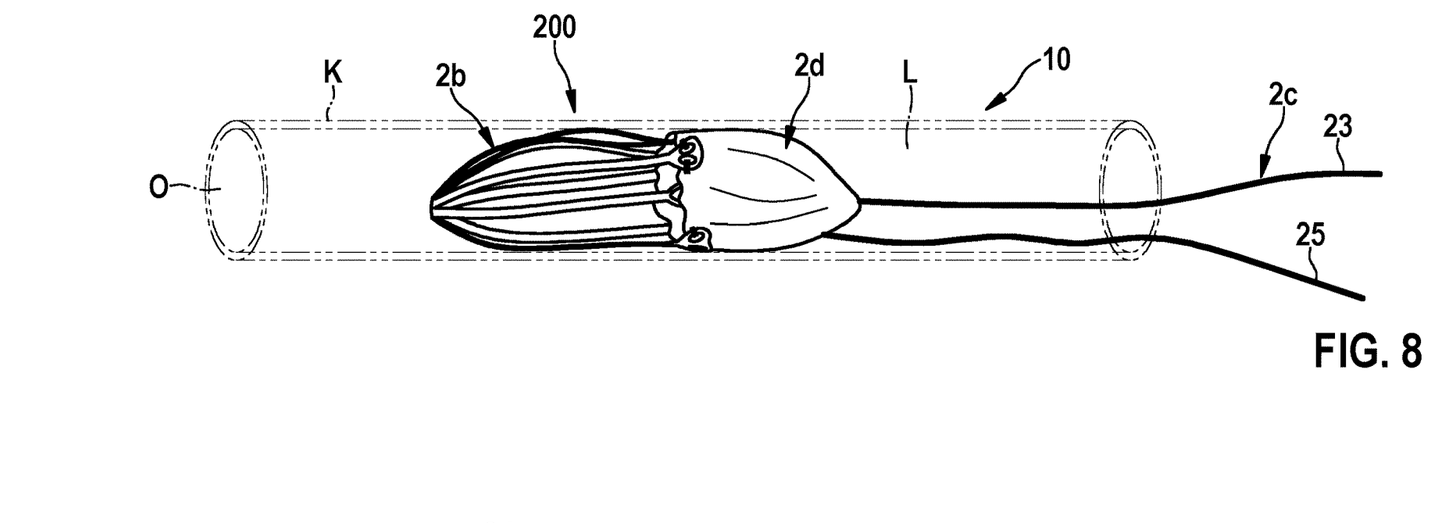
FIG. 8 shows a view of a closure implant arranged in a lumen of a catheter.
Figure 9:
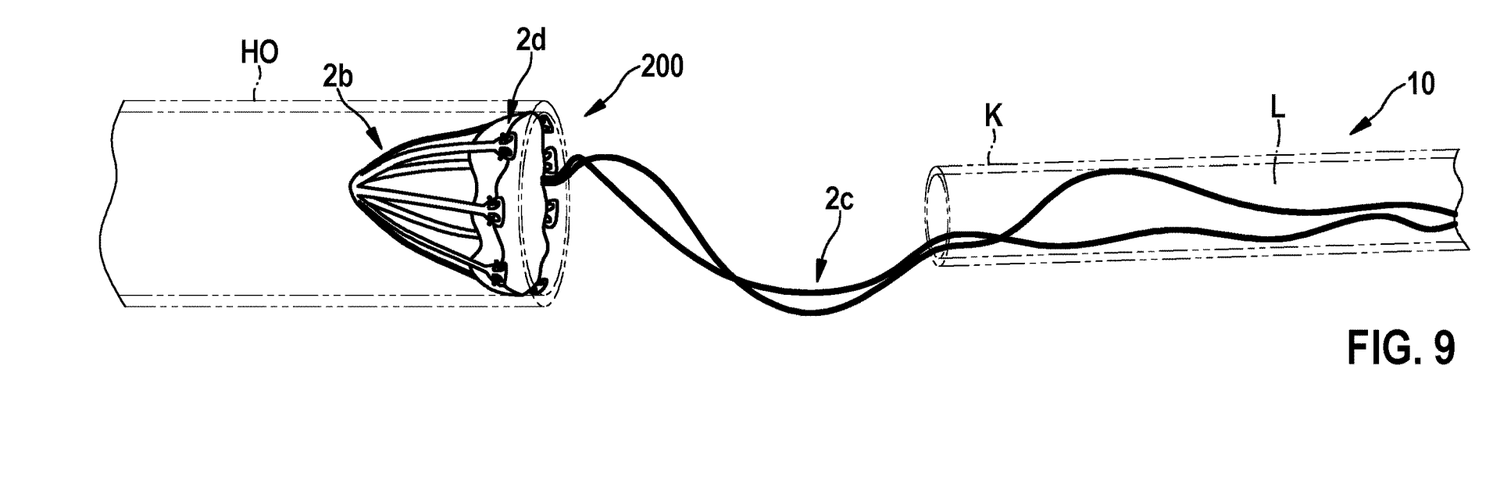
FIG. 9 shows a view of the release of the closure implant in the atrial appendage.
Figure 10:
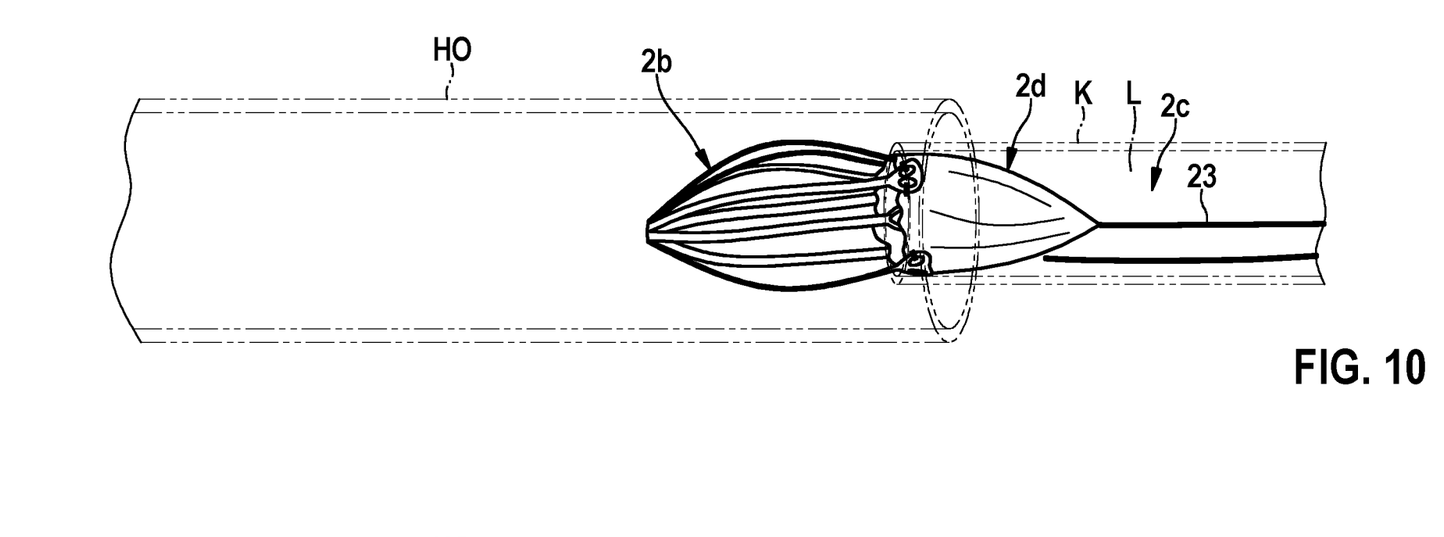
FIGS. 10 and 11 show the pulling of the closure implant back into the catheter lumen (what is known as recapturing)
Figure 11:
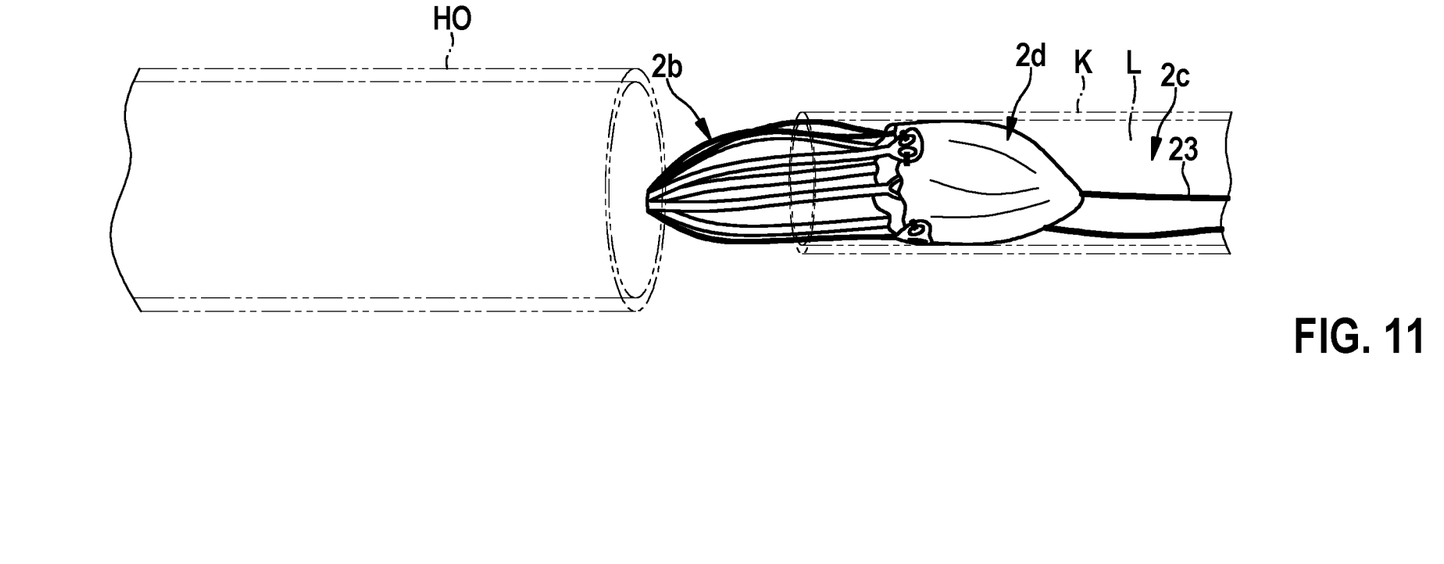
Figure 12:
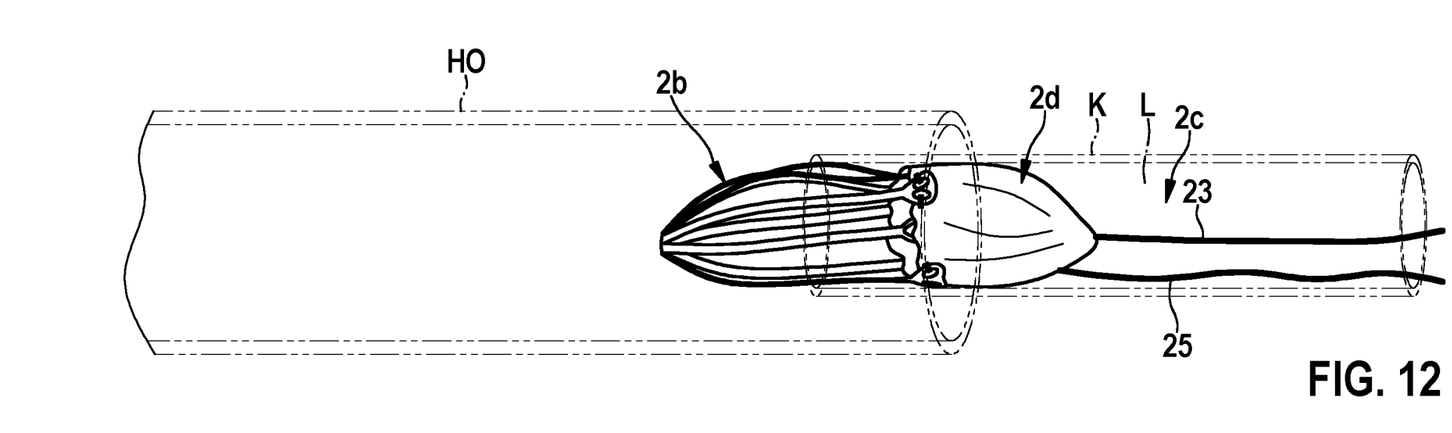
FIGS. 12 and 13 shows the renewed release of the closure implant in the left atrial appendage.
Figure 13:
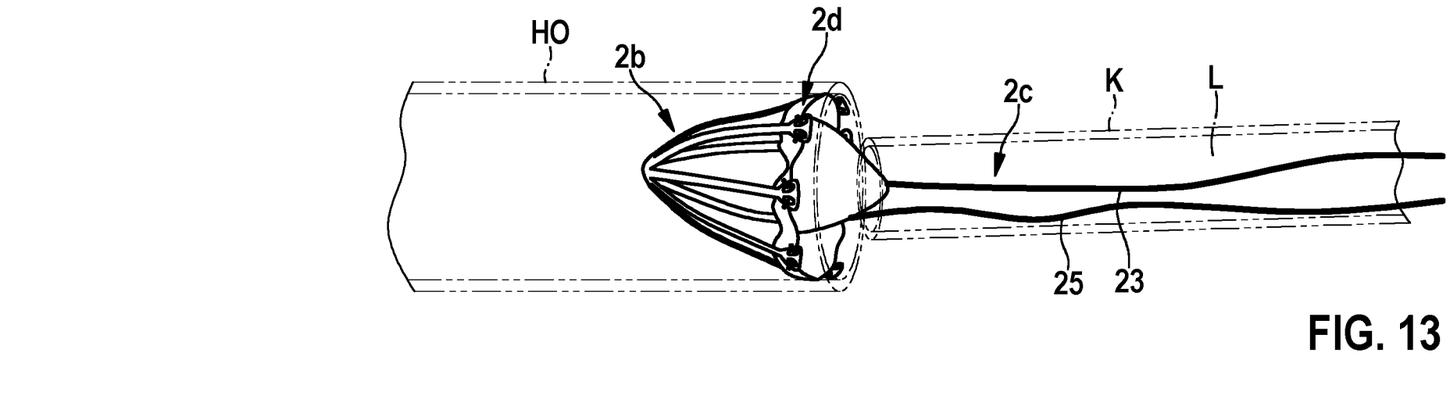
Figure 14:
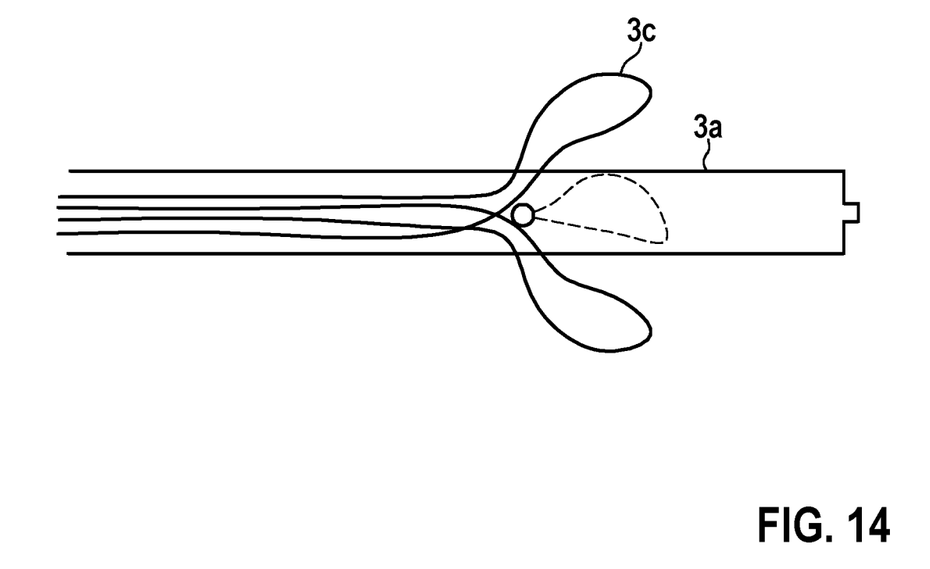
FIG. 14 shows a schematic side view of a further device for positioning and releasing a closure implant.
Figure 15:
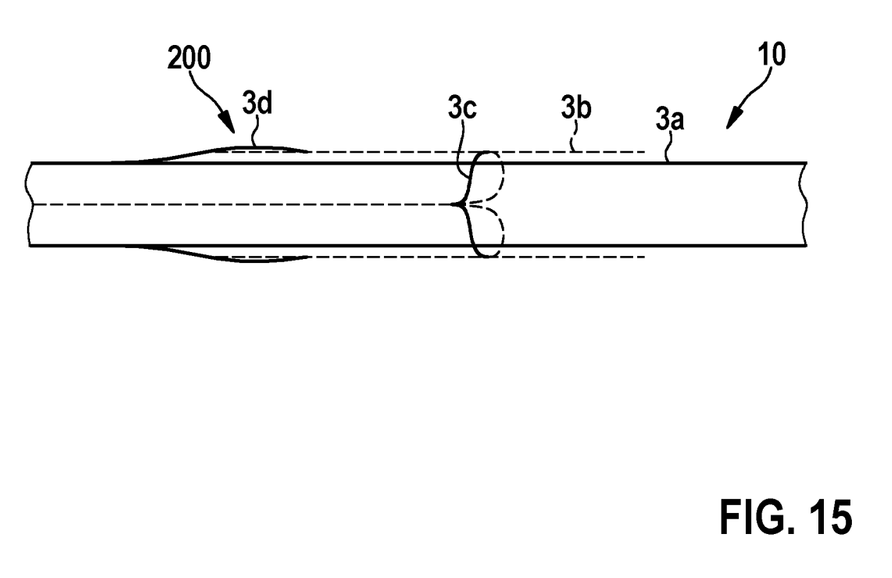
FIG. 15 shows a schematic sectional view of the device according to FIG. 14 with closure implant/stent framework in the compressed state.
Figure 16:
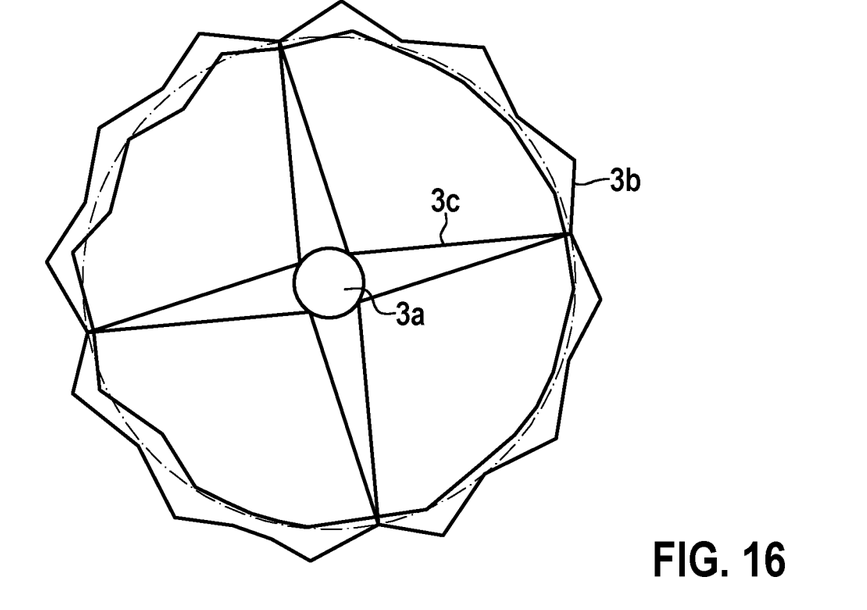
FIG. 16 shows a further schematic sectional view (perpendicular to the axial direction) of the device shown in FIGS. 14 and 15 with expanded stent framework.
Figure 17:
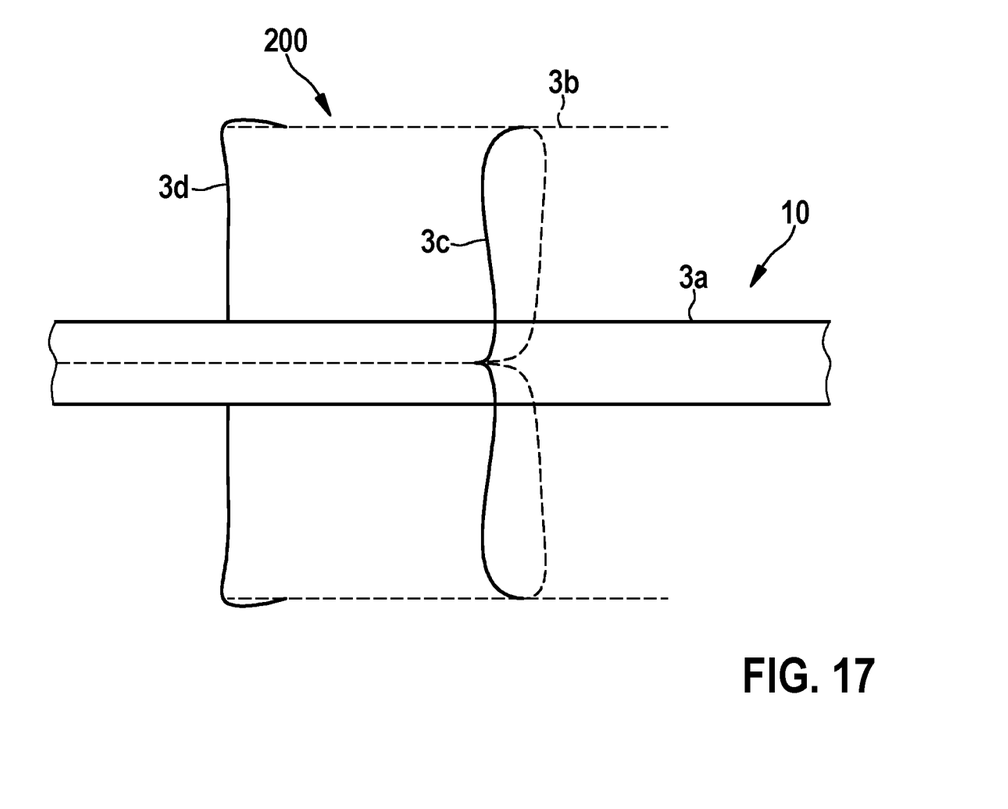
FIG. 17 shows a further schematic sectional view of the device shown in FIGS. 14 to 16 with expanded stent framework.

The struts 20 can also each have, at the second end portions 22, a protrusion 2f of at least 1.5 mm in order to anchor the stent framework 2b in the ostium of the atrial appendage HO (see FIGS. 6 and 7).

According to one example of the invention, the material layer 2d consists of a fabric, in particular of a textile fabric formed of polyester threads (for example Dacron®), with a mesh porosity which in particular is not greater than 0.15 mm.

Whereas the pulling element 2c is guided through the material layer 2d starting from the first end 23, the other second end 25 is guided laterally past the material layer 2d or the stent framework, so that the pulling element 2c here as well is guided laterally past the material layer 2d into the space of the atrium.

Following implantation (see FIGS. 8 and 9), it is now possible to pull the closure implant 200 back into the catheter K by means of the pulling element 2c by pulling on the first end 23, wherein the thickened portion 24 pulls the material layer 2d and therefore the closure implant 200 as a whole (FIGS. 10 and 11), and to start a new implantation attempt (FIGS. 12 and 13) or to abort the procedure, as appropriate.

Following successful implantation, the entire pulling element 2c with the thickened portion 22 can be pulled out between the ostium of the atrial appendage HO and the material layer 2d of the closure implant (also referred to as an occluder) by pulling the lateral second end 25 of the pulling element 2c. A decoupling of the closure implant 200 from the catheter K is ensured hereby.

It can also be provided that the struts 20 each have a right-hand curvature and then a left-hand curvature starting from the corresponding first end portion 21, as is shown in FIGS. 6 and 7.

This results in a goblet-like shape of a virtual envelope of the expanded stent framework 2b. In particular, a greater cylindrical part of the system or stent framework 2b and an accordingly greater covering between the closure implant 200 and the atrial appendage HO are thus obtained. Furthermore, a short extent into the atrial appendage OH is provided (reduction of puncturing risk, and flat anatomies can be better replicated).

The pulling element 2c can be formed from nylon or can comprise nylon (or can comprise one or more threads made of nylon). Other comparable biocompatible fibres formed of a multi- or monofilament are also conceivable. The thickened portion 24 can have a body made of plastic.

FIGS. 14 to 17 also show a further alternative device 10 for positioning and releasing a closure implant 200 for closing the left atrial appendage HO, wherein here as well the controlled release of the closure implant 200 is not provided with the aid of a pull-back system, as is otherwise usual, but instead with the aid of pulling elements 3c or a cord pull system 3c. To this end a cylindrical stent framework 3b is preferably collapsed (for example see FIG. 18) with the aid of at least one pulling element (for example a cord or thread) 3c and is introduced through a port. At the implantation site the stent 3b sitting on the catheter 3a is released by adjusting the pulling elements 3c or the cord pull system 3c (see FIG. 17) and remains connected thereto. The pulling elements 3c enable a controlled, gradual release of the implant 200, a simple monitoring of the fixing of the closure implant 200 following the release, and re-positioning thereof as appropriate. The cord pull system or the pulling elements 3c is/are removed for the final release.

In particular, the scent framework 3b can be crimped or compressed to a diameter of, for example, 12 Fr with the aid of a cord pull system consisting of four pulling elements 3c according to FIGS. 14 to 17. In this state the closure implant 200 is advanced with the aid of the catheter 3a to the intended site within the left atrial appendage HO and is released slowly and in a controlled manner (see FIG. 17) by relaxing the pulling elements 3c (for example threads or cords). In order to ensure a complete closure of the atrial appendage HO, a material layer or cover 3d is provided, which is fixed on the proximal side of the stent framework 3b, for example by stitches. The material layer 3d for example consists of a textile fabric (for example of polyester threads, in particular Dacron®) with a mesh porosity which in particular is not greater than 0.1 mm.

Figure 18:
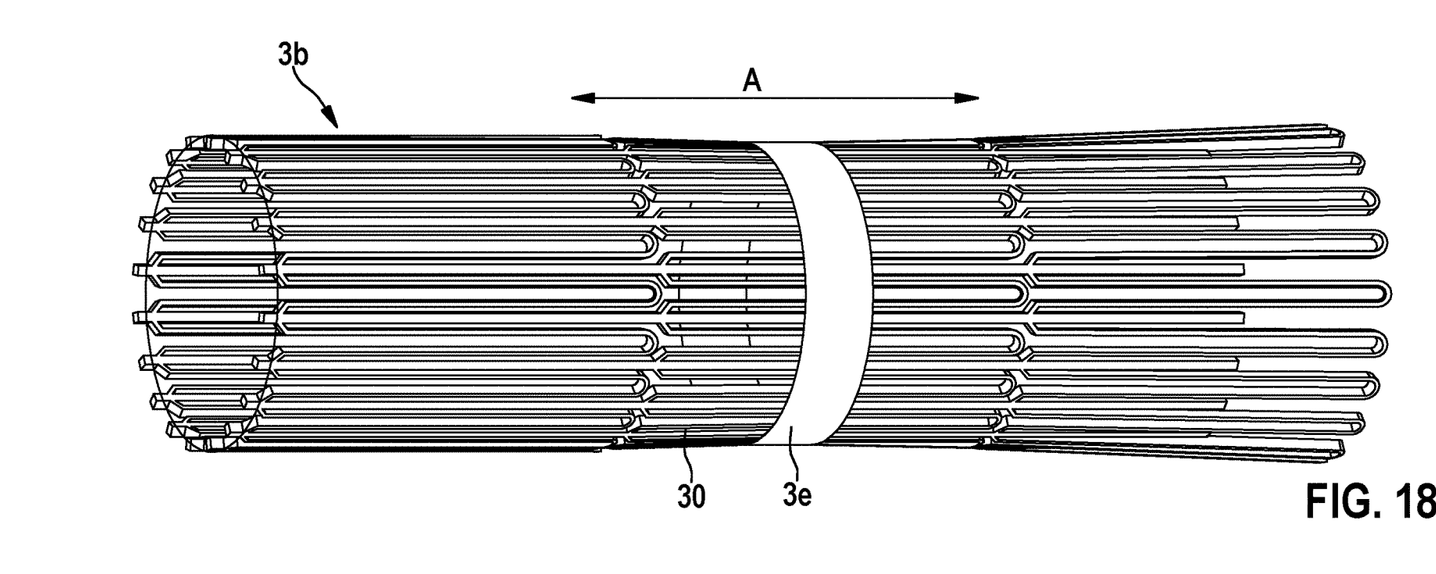
FIG. 18 shows a stent framework of the kind in FIGS. 14 to 17 compressed by means of a peripheral pulling element.

The closure implant 200 or the stent framework 3b can be formed in principle in accordance with FIG. 18 in such a way that only a centrally running pulling element (for example thread or cord) 3e, which for example runs centrally around the stent 3b in the peripheral direction, is sufficient to crimp or compress the stent framework 3b so as to reduce the overall length (along the axial direction A) to a diameter of, for example, 12 Fr.

Figure 19:
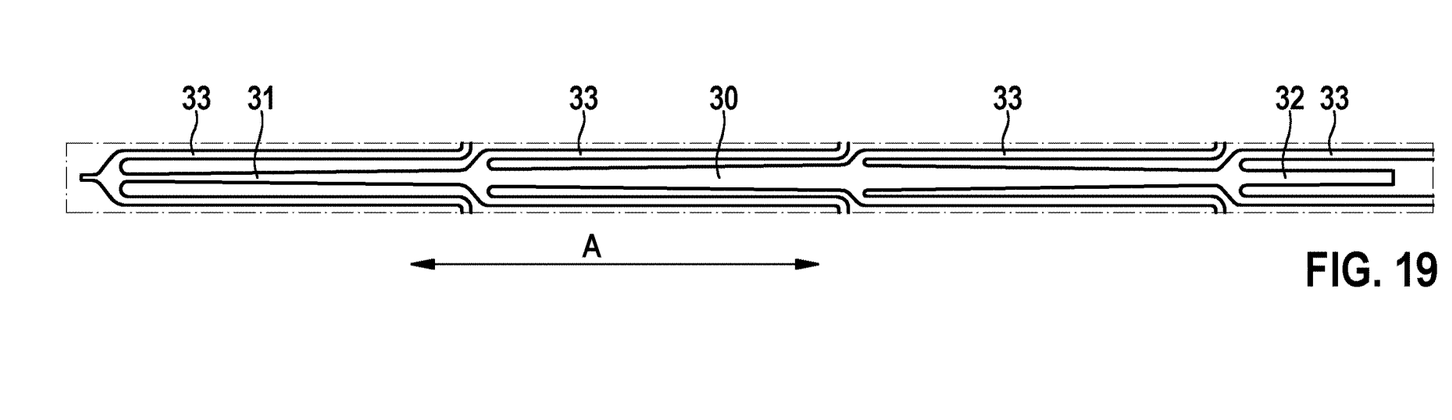
FIG. 19 shows an axial bar of the stent framework shown in FIG. 18 and portions of stent half-cells, by means of which the bar is connected to bars that are adjacent in the peripheral direction of the stent framework.

This is achieved in accordance with FIG. 19 by the continuous bar 30 of the stent framework 3b running lengthwise in the stent axis or in the axial direction A. The bars 30 are connected to one another by stent half-cells 33 provided in the peripheral direction between the bars 30, wherein the half-cells 33 preferably have a width that is 50% smaller than the width of the bars 30.

The bars 30 preferably also taper towards both ends 31, 32, so that the greatest width of the bars 30 is in the middle of the stent and in particular is 50% greater than the width at the respective bar ends 31, 32. This makes it possible for the force acting in the middle (transferred to the bars by the cord pull system 3c or the pulling elements 3c, see FIG. 16) to be great enough to displace the two bar ends 31, 32, similarly to the bar middle, relative to the centre point of the longitudinal axis A of the stent 3b.

It will be apparent to those skilled in the art that numerous modifications and variations of the described examples and embodiments are possible in light of the above teaching. The disclosed examples and embodiments are presented for purposes of illustration only. Other alternate embodiments may include some or all of the features disclosed herein. Therefore, it is the intent to cover all such modifications and alternate embodiments as may come within the true scope of this invention.

What is claimed is:

1. A device for closing the left atrial appendage, comprising
a closure implant for closing the left atrial appendage, comprising a self-expanding stent framework, which can be automatically expanded from a compressed state into an expanded state, and wherein the closure implant has a flexible material layer fixed to the stent framework, wherein the material layer in the expanded state of the stent framework is stretched,
a catheter with a lumen for receiving the closure implant in the compressed state of the stent framework, wherein the closure implant can be released from the lumen by being slid out, and in so doing the stent framework can be transferred into the expanded state, and
a flexible and elongate pulling element extending through the flexible material layer so that the closure implant can be drawn back into the lumen of the catheter by pulling the pulling element, which pulls the flexible material layer to cause the stent framework to be transferred into the compressed state.

2. The device according to claim 1, wherein the pulling element comprises a cord or a thread.

3. The device according to claim 1, wherein the material layer is a fabric.

4. The device according to claim 1, wherein the stent framework comprises a plurality of struts, wherein the struts each have a first end portion and an opposite second end portion, and wherein the first end portions of the struts are connected to one another, and wherein the second end portions are each connected to a peripheral edge region of the material layer.

5. The device according to claim 4, wherein the peripheral edge region at least partially covers the second end portions of the struts.

6. The device according to claim 4, wherein the struts each have, at the second end portions, a protrusion for anchoring the stent framework in the ostium of the atrial appendage (HO).

7. The device according to claim 6, wherein the protrusion is at most 1.5 mm long.

8. The device according to claim 4, wherein the struts each have a right-hand curvature and then a left-hand curvature starting from the corresponding first end portion.

9. A device for closing the left atrial appendage, comprising
a closure implant for closing the left atrial appendage, comprising a self-expanding stent framework, which can be automatically expanded from a compressed state into an expanded state, and wherein the closure implant has a flexible material layer fixed to the stent framework, wherein the material layer in the expanded state of the stent framework is stretched,
a catheter with a lumen for receiving the closure implant in the compressed state of the stent framework, wherein the closure implant can be released from the lumen by being slid out, and in so doing the stent framework can be transferred into the expanded state, and
a flexible and elongate pulling element fixed to the flexible material layer so that the closure implant can be drawn back into the lumen of the catheter by pulling the pulling element, which causes the stent framework to be transferred into the compressed state, wherein the pulling element has a first and a second end, wherein the pulling element has a thickened portion between the two ends, so that the pulling element can be pulled out completely from the material layer by pulling on the second end, and so that the thickened portion impacts against the material layer when the pulling element is pulled at the first end, so that the closure implant can be pulled back into the lumen of the catheter when the closure implant is released.

10. A device for closing the left atrial appendage, comprising
a closure implant for closing the left atrial appendage, comprising a self-expanding stent framework, which can be automatically expanded from a compressed state into an expanded state, and wherein the closure implant has a flexible material layer fixed to the stent framework, wherein the material layer in the expanded state of the stent framework is stretched,
a catheter with a lumen for receiving the closure implant in the compressed state of the stent framework, wherein the closure implant can be released from the lumen by being slid out, and in so doing the stent framework can be transferred into the expanded state, and a flexible and elongate pulling element fixed to the flexible material layer so that the closure implant can be drawn back into the lumen of the catheter by pulling the pulling element, which causes the stent framework to be transferred into the compressed state, wherein stent framework comprises a plurality of struts, wherein the struts each have a first end portion and an opposite second end portion, and wherein the first end portions of the struts are connected to one another, and wherein the second end portions are each connected to a peripheral edge region of the material layer, and wherein the second end portions in the compressed state of the stent framework have a shorter spacing from one another than in the expanded state of the stent framework, in which the second end portions are distanced from one another in such a way that the material layer is stretched.

11. A device for closing the left atrial appendage, comprising
a closure implant for closing the left atrial appendage, comprising a self-expanding stent framework, which can be automatically expanded from a compressed state into an expanded state, and wherein the closure implant has a flexible material layer fixed to the stent framework, wherein the material layer in the expanded state of the stent framework is stretched, a catheter with a lumen for receiving the closure implant in the compressed state of the stent framework, wherein the closure implant can be released from the lumen by being slid out, and in so doing the stent framework can be transferred into the expanded state, and a flexible and elongate pulling element fixed to the flexible material layer so that the closure implant can be drawn back into the lumen of the catheter by pulling the pulling element, which causes the stent framework to be transferred into the compressed state, wherein stent framework comprises a plurality of struts, wherein the struts each have a first end portion and an opposite second end portion, and wherein the first end portions of the struts are connected to one another, and wherein the second end portions are each connected to a peripheral edge region of the material layer, and wherein the second end portions each have at least one recess in the form of an eyelet, wherein the peripheral end region of the material layer is connected to the at least one recess of each second end portion by one thread per recess.

12. A device for closing the left atrial appendage, comprising a closure implant for closing the left atrial appendage, comprising a self-expanding stent framework, which can be automatically expanded from a compressed state into an expanded state, the stent framework comprising struts having a common base and that extend way from the common base to opposite end portions;

a flexible material layer attached by its peripheral edge regions to the opposite end portions of the struts, wherein the material layer in the expanded state of the stent framework is stretched between the opposite end portions of the struts to form a circular surface, a catheter with a lumen for receiving the closure implant in the compressed state of the stent framework, wherein the closure implant can be released from the lumen by being slid out, and in so doing the stent framework can be transferred into the expanded state, and     a flexible and elongate pulling element that engages the flexible material layer and is structured to pull the flexible material layer away from the common base and thereby pull the second end portions of the struts together when pulled from a first end of the pulling element and to pull through and out of the flexible material layer when pulled from a second end of the pulling element.

13. The device according to claim 12, wherein the pulling element comprises a cord or a thread.

14. The device according to claim 13, wherein the cord or thread comprises a drop-shaped thickened portion wherein the drop tapers in the direction of the second end of the pulling element.

* * * * *